(12) United States Patent
Duerr

(10) Patent No.: US 6,578,430 B1
(45) Date of Patent: Jun. 17, 2003

(54) SERVICE LIFE INDICATOR FOR HIGHLY STRESSED LIGHT-WEIGHT STRUCTURES

(75) Inventor: Werner Duerr, Ahausen (DE)

(73) Assignee: Dornier GmbH, Friedrichshafen (DE)

( * ) Notice: Subject to any disclaimer, the term of this patent is extended or adjusted under 35 U.S.C. 154(b) by 0 days.

(21) Appl. No.: 09/556,970

(22) Filed: Apr. 24, 2000

(30) Foreign Application Priority Data

Apr. 22, 1999 (DE) .......................................... 199 18 219

(51) Int. Cl.[7] ................................................. G01D 1/00
(52) U.S. Cl. ....................................................... 73/787
(58) Field of Search ........................ 73/787, 799, 88 R, 73/762, 755, 88.5 R, 795, 775; 29/407

(56) References Cited

U.S. PATENT DOCUMENTS

| | | | |
|---|---|---|---|
| 3,136,154 A | 6/1964 | Christensen | 73/88 |
| 4,164,874 A | 8/1979 | Cassatt et al. | 73/799 |
| 4,409,841 A | * 10/1983 | Archer | 73/760 |
| 4,639,997 A | * 2/1987 | Brull | 29/407 |
| 5,237,875 A | 8/1993 | de la Veaux | 73/775 |
| 5,319,982 A | 6/1994 | Creager | 73/762 |
| 5,520,055 A | 5/1996 | Fussinger | 73/762 |
| 5,614,680 A | * 3/1997 | Fussinger | 73/799 |

FOREIGN PATENT DOCUMENTS

DE 43 38 850 5/1995

* cited by examiner

Primary Examiner—Hezron Williams
Assistant Examiner—Octavia Davis
(74) Attorney, Agent, or Firm—Crowell & Moring LLP

(57) ABSTRACT

The invention relates to a service life indicator for monitoring structures, such as pioneering bridges, which are designed with a limited fatigue strength and whose service life is therefore limited. A service life indicator for monitoring structures, such as pioneering bridges designed with a limited fatigue strength and consequently limited service life, is provided. The service life indicator includes a strip of material as a test piece, having at least one hole arranged off-center in the test piece and a notch extending from an edge of the hole in a direction of an edge of the test piece for determining material fatigue. The notch extends to a nearest edge of the test piece and includes two mutually opposite grooves having the same cross-sectional shape that can be one of round, elliptical, oval, v-shaped and trapezoidal in cross-section.

10 Claims, 3 Drawing Sheets

SERVICE LIFE INDICATOR FOR HIGHLY STRESSED LIGHT-WEIGHT STRUCTURES

BACKGROUND AND SUMMARY OF THE INVENTION

This application claims the priority of German Application No. 199 18 219.1, filed Apr. 22, 1999, the disclosure of which is expressly incorporated by reference herein.

The invention relates to a service life indicator for highly stressed lightweight structures, The service life indicator has a strip of material as the test piece, which has at least one hole arranged off-center in the test piece and a notch extending from the edge of the hole in the direction of the edge of the test piece. The test piece serves as the device for determining the material fatigue. A service life indicator of this type is known from German Patent Document DE 43 38 850 A1.

From U.S. Pat. No. 3,136,154, a strip-shaped fatigue indicator is known which has holes or notches and which is mounted on the structure to be examined.

Modern military pioneering bridges are progressive lightweight aluminum constructions, characterized by a high material utilization factor, with—in comparison to civilian bridges—very low crossing numbers and high loads. The relatively low number of guaranteed crossings requires one to record the number of crossings which occur as a function of the crossing load and the laid span in order to obtain a reliable indication before reaching the permitted service life and a measurement of the remaining surface life. This recording was previously carried out by keeping a log-book.

The following is known as prior art with respect to service life indicators of metallic structures of this type, in addition to the above-mentioned log-book. The monitoring of the structure by means of wire strain gauges, meters and a corresponding electronic analyzing system; the monitoring of the structure by means of glued-on metal foils which change their reflection behavior as the result of any extension experienced; a device which is mounted on the structure to be monitored and into which small, differently notched, test pieces are clamped.

It is disadvantageous that these indicators either: (1) require electric energy; (2) have no long-term-stable connection to the structure; (3) are too sensitive and too expensive for a constant use in the open air; and/or (4) only insufficiently take into account additional marginal conditions, such as the deviation of material and environmental influences.

The object of the invention is to provide a robust and reliably readable fatigue indicator for light-weight structures.

Other objects, advantages and novel features of the present invention will become apparent from the following detailed description of the invention when considered in conjunction with the accompanying drawings.

DETAILED DESCRIPTION OF THE DRAWINGS

Figure 1:
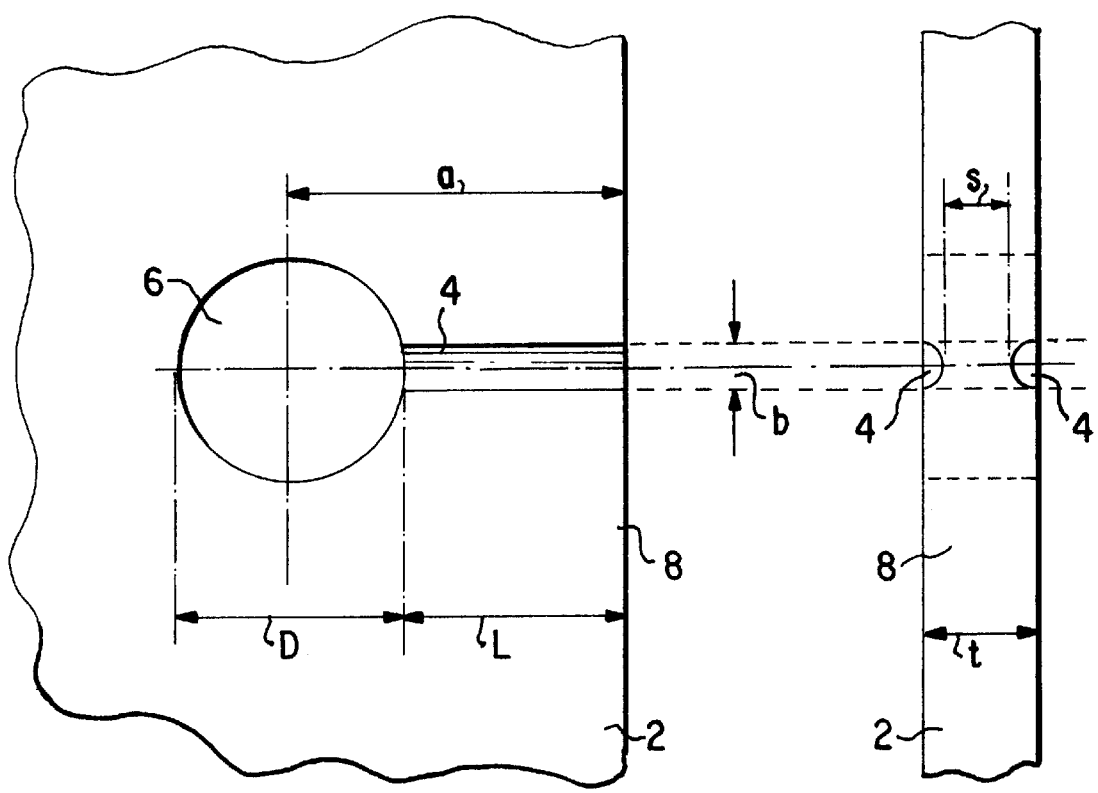
FIG. 1 is a schematic diagram of a fatigue indicator according to the invention.
Figure 1A:
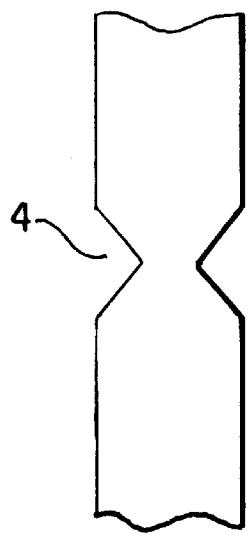
FIGS. 1a and 1b illustrate different cross-sections of the notch grooves according to the invention.
Figure 1B:
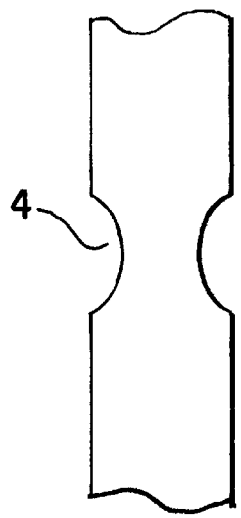

The following details are illustrated in the schematic diagram of FIG. 1. A test piece is shown 2 in a top view (left side) and a lateral view (right side). A bore 6 is provided in the test piece having a bore diameter D and a distance a of the bore 6 from the lateral edge 8 of the test piece. The thickness t of the test piece 2 is shown in the lateral view. The width b of the notch 4, the ligament thickness S. and the ligament length L are also shown in FIG. 1.

Figure 2:
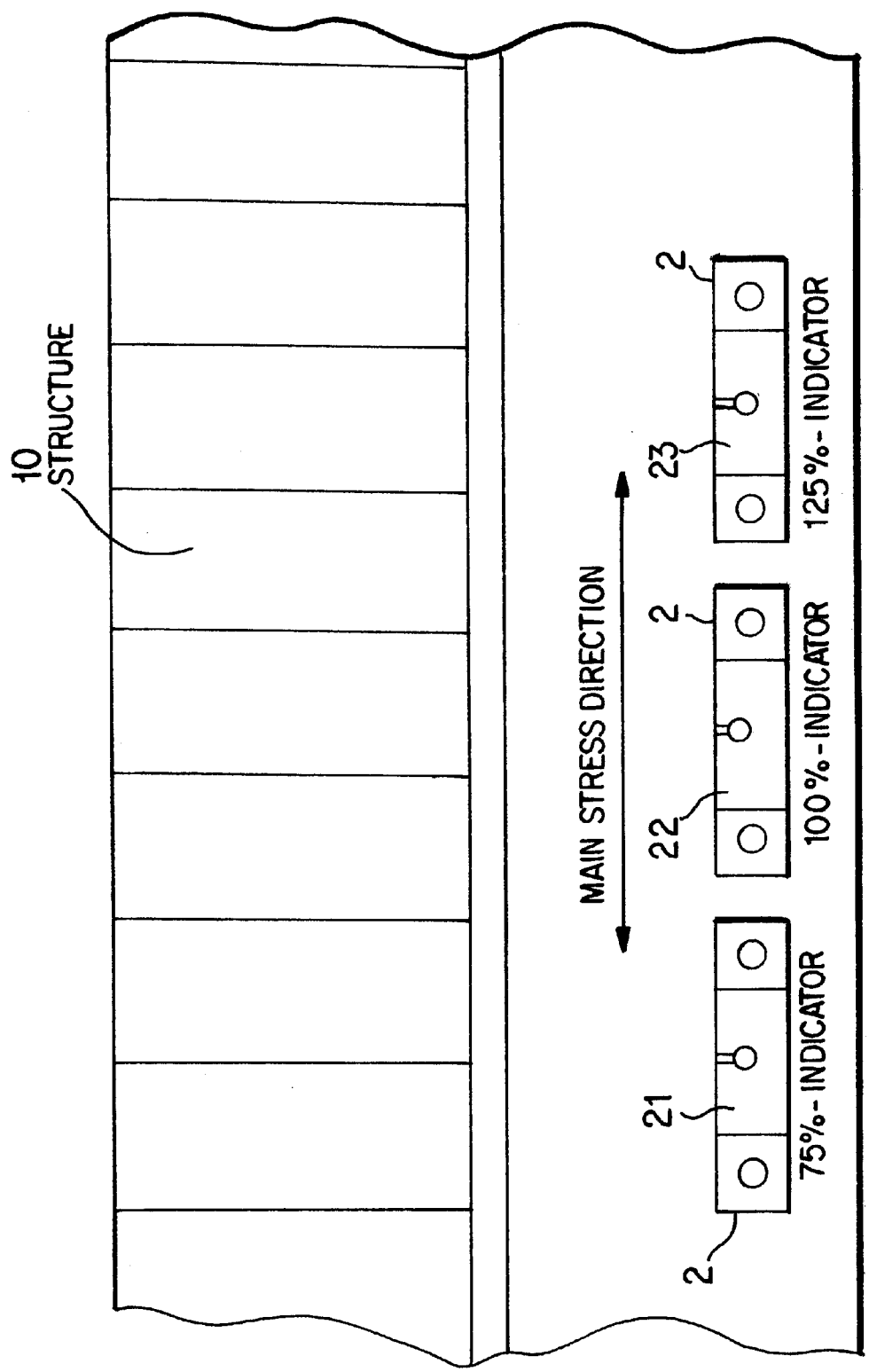
FIG. 2 is an example of the mounting of a group of fatigue indicators according to the invention.

The principle of the "load counter" according to the invention is based on the mounted fracture-mechanical test pieces 2, which are made of identical material as the structure 10 (FIG. 2) to be monitored and have notches 4 of different sharpnesses. The point in time when the different test pieces start to tear 12 (FIG. 4) or tear through results in a measurement of the load history "experienced" by the structure 10. It identical, arbitrarily exchangeable individual sections of a variably composed structure 10 are provided with indicators 2, the service life of each Individual section can be recorded as a function of the installation site and the load amount.

The test pieces 2 are fatigue samples which are adapted to the existing stress level, with respect to the sample type, the point of concentration of their "service life" concerning the fatigue or crack formation phase and not the rate of crack growth. The notch shape 4 according to the invention avoids a concentration of stress at the notch tip which, in a very plastified manner, influences the starting phase of the crack 12 and leads to a considerable deviation of the starting point in time of the crack. The notch shape (round, elliptical, oval, v-shaped, trapezoidal cross-sections) according to the invention avoids this disadvantage by the design as the "fatigue sample" with a three-dimensional stress condition in the notch 4, whose stress concentration is no higher than the highest concentration of the component to be monitored.

As illustrated in FIGS. 1 to 4, this is achieved by the combination of an eccentrically perforated strip of material forming the test piece 2, with an additional lateral notch 4 between the bore 6 and the sample edge 8 The bore 6 in the proximity of an edge 8 produces a notch factor $\alpha k$ similar to the highest notch factor of the structure 10 to be monitored, while the lateral notch 4 results in an increased three-dimensional stress condition in the ligament. The three-axis stress condition prevents a plastifying in the notch root and leads to a reliable, almost uniform fatigue of the residual cross-section in the full length of the ligament, as the result of which the notch root will be completely torn through 12 after a short crack growth phase.

The arrangement of this notch shape 4 causes a reliable narrow-band tearing-through of the ligament (FIG. 2) when a predetermined endurance has been reached. In this case, the specific properties of the material as well as environmental influences, such as corrosion and temperature cycles, are included in the result because the test pieces 2 are manufactured of an identical material (charge, heat treatment, deformation, grain orientation) and are subjected to the same environmental influences as the structure.

The test pieces 2 are trimmed to the structure 10 to be monitored in that their geometry is adapted to the used material, to the structure wall thickness, to the stress level, to the stress ratio and to the endeavored loading range. Because of this adaptability, the indicator does not have to be mounted in the area of the greatest stress but can be mounted in more favorable areas corresponding to the situation, without additionally weakening critical points. In order to obtain a larger indicating range and cover the deviations of the test pieces, as a rule, three indicators 21, 22, 23 (FIG. 2) having notches constructed with different sharpnesses are arranged behind one another, so that they supply an indication at, for example, 75%, 100% and 125% of the expected service life. The actual failing of the structure will then later take place corresponding to the probability/reliability of the characteristic values of the material on which their dimensioning was based. The linking of the indicators to the structure 10 to be monitored takes place by means of special fastening elements in a force-locking and form-locking manner or, in the case of thin-walled structures, by means of high-strength shear tension rivets.

Figure 3:
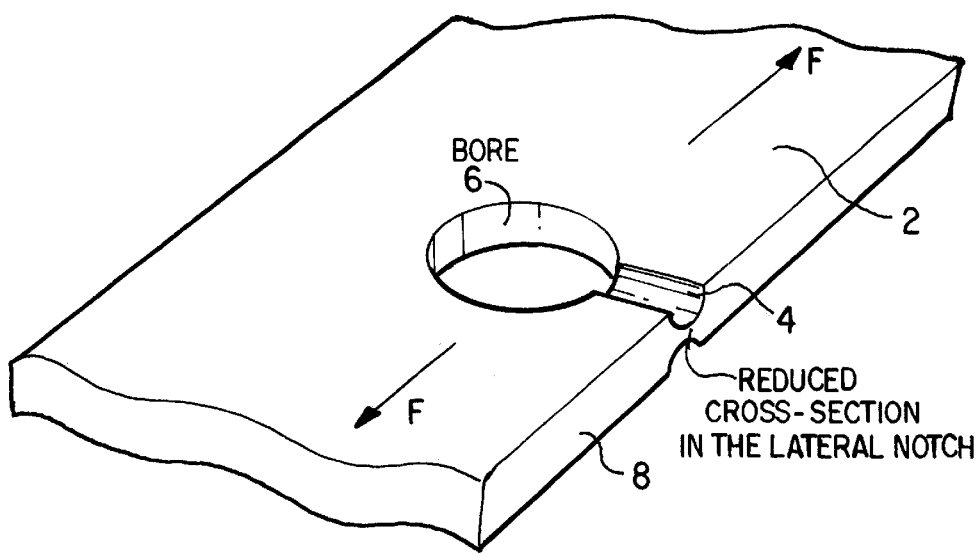
FIGS. 3 and 4 are axonometric representations of the fatigue indicator according to the invention.
Figure 4:
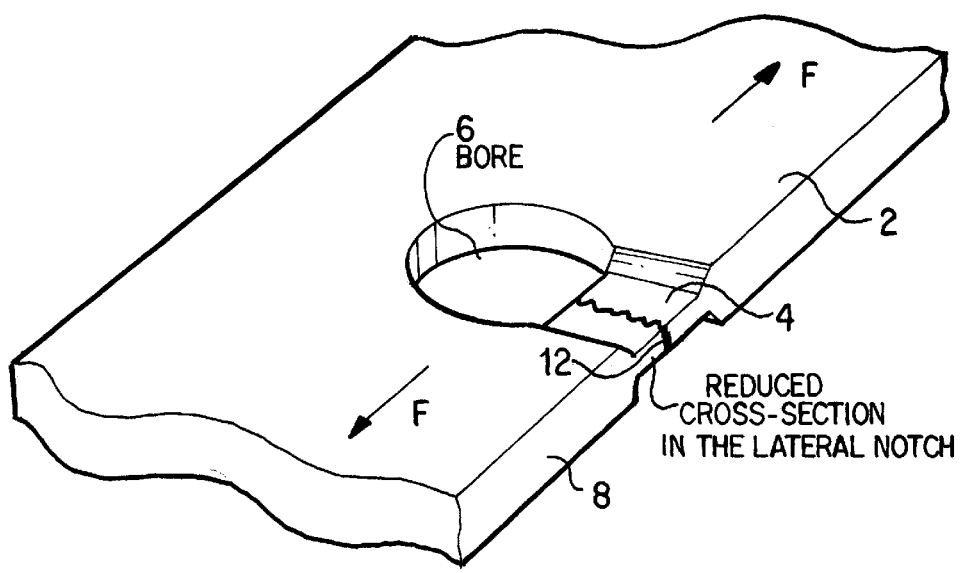

As the result of the proven validity of the damage accumulation theory according to Palmgreen-Miner, also the loadings with a lower or higher load level are detected close to reality corresponding to their damage equivalent. Sequence influences because of load cycles of different load amounts as well as the influence of the one-time crossing of a certain overload are minimized in that the plastifying of the ligament is avoided by the selection of the notch geometry (FIGS. 3, 4).

The ligaments s of the individual test pieces 2 are scanned within the scope of control inspections by means of a special eddy current probe, and possibly torn-apart ligaments are detected. Crack detection by means of the eddy current reliably takes place through paint layers and dirt; for narrowing the loading indicating range, the starting crack of a ligament can even be detected. The detected finding will then be transmitted into an analyzing diagram which supplies a conclusion concerning the experienced load history of the structure. Naturally, providing that there is a corresponding accessibility and there are corresponding preparation expenditures, any other suitable crack testing process can be used for detecting the torn-apart ligaments.

The service life indicator according to the invention provides the following advantages: (1) robust nature; (2) no external energy required; (3) "true" fatigue indicator, no crack growth indicator; (4) low deviation because of identical material and short crack growth phase; (5) notch factor similar to that of the structure to be monitored; (6) crack in the indicator will never endanger the structure to be monitored; (7) flexible in its mounting; no additional weakening of the structure; (8) adaptable with respect to stress level and indicating range; (9) advantageous with respect to manufacturing and therefore reasonably priced; and (10) simply and reliably readable.

What is claimed is:

1. Service life indicator for highly stressed light-weight structures, comprising:
    a strip of material as a test piece, having at least one hole arranged off-center in the test piece and a notch extending from an edge of the hole in a direction of an edge of the test piece, for determining material fatigue;
    wherein the at least one hole is a bore and the notch extends to a nearest edge of the test piece;
    wherein the notch in the test piece comprises two mutually opposite grooves in the strip of material having the same cross-sectional shape; and
    wherein the grooves have one of a round, elliptical, oval, v-shaped, and trapzioal cross-section.

2. Service life indicator according to claim 1, wherein the bore in the test piece has one of a circular, oval, and elliptical cross-section.

3. Service life indicator according to claim 1, wherein the test piece is formed of a material identical to that or a structure being monitored.

4. Service life indicator according to claim 1, wherein the grooves have a rounded cross-section.

5. Service life indicator according to claim 1, wherein the grooves have an elliptical cross-section.

6. Service life indicator according to claim 1, wherein the grooves have an oval cross-section.

7. Service life indicator according to claim 1, wherein the grooves have a v-shaped cross-section.

8. Service life indicator according to claim 1, wherein the grooves have a trapezoidal cross-section.

9. A service life monitoring system, comprising:
    a monitorable structure made of a first material; and
    a service life indicator mounted on said monitorable structure, said service life indicator comprising a strip of test piece material, having at least one hole in the form of a bore arranged off-center in the test piece material and a notch extending from an edge of the bore to a nearest edge of the test piece material, the notch comprising two mutually opposite grooves in the strip of material having the same cross-sectional shape, said grooves having one of a round, elliptical, oval, v-shaped and trapezoidal cross-section.

10. The system according to claim 9, wherein the test piece material is the same as the first material of the monitorable structure.

* * * * *